United States Patent [19]

Hayes et al.

[11] Patent Number: 5,726,049
[45] Date of Patent: Mar. 10, 1998

[54] ENZYMATIC PREPARATION OF MONIC ACIDS

[75] Inventors: Esme Faith Hayes, Worthing; John Thomas Sime, Dorking; Stefan Roland Woroniecki, Horsham; David Alan Yeandle, Lancing, all of England

[73] Assignee: SmithKline Beecham p.l.c., Brentford, England

[21] Appl. No.: 578,587

[22] PCT Filed: Jun. 21, 1994

[86] PCT No.: PCT/EP94/02030

§ 371 Date: Feb. 15, 1996

§ 102(e) Date: Feb. 15, 1996

[87] PCT Pub. No.: WO95/02064

PCT Pub. Date: Jan. 19, 1995

[30] Foreign Application Priority Data

Jul. 3, 1993 [GB] United Kingdom ............... 9313796

[51] Int. Cl.$^6$ .................. C12N 9/14; C12N 9/16
[52] U.S. Cl. ............... 435/136; 435/195; 435/196; 435/197; 435/911
[58] Field of Search ....................... 435/195, 196, 435/197, 136, 911

[56] References Cited

U.S. PATENT DOCUMENTS 4,284,570  8/1981  Rogers et al. ............... 549/417

FOREIGN PATENT DOCUMENTS 0 003 069  7/1979  European Pat. Off. .
0180285  6/1989  Japan .
1 587 059  3/1981  United Kingdom .

OTHER PUBLICATIONS

Freer et al. Proceedings 3$^{rd}$ Intl. Symp., Elsevier, 1988 pp. 295–298.
Sime et al. Tet. Lett. Vol. 28(43) pp. 5169–5172 1987.
Mantle et al. Appl. Microbiol. Biotechnol. vol. 33, pp. 709–711 1990.

Primary Examiner—Leon B. Lankford, Jr.
Assistant Examiner—Christopher R. Tate
Attorney, Agent, or Firm—William T. King; Edward T. Lentz

[57] ABSTRACT

A process for the production of monic acids which comprises contacting a corresponding pseudomonic acid or an ester thereof with a hydrolase enzyme from a suitable microorganism, in particular Streptomyces sp.

3 Claims, No Drawings

ENZYMATIC PREPARATION OF MONIC ACIDS

The present invention relates to a process for the conversion of pseudomonic acids and esters thereof to the corresponding monic acid.

Pseudomonic acids have well known antibacterial properties. Known pseudomonic acids include the tetrahydropyranyl compounds pseudomonic acid A (Nature, 1971, 234, 416; JCS Perkin Trans. I, 1977, 294), pseudomonic acid B (JCS Perkin Trans. I, 1982, 2827), pseudomonic acid C (JCS Perkin Trans. I 1982, 2827) and pseudomonic acid D (JCS Perkin Trans. I, 1983, 2655).

In particular, the present invention provides a process for the conversion of pseudomonic acid A (mupirocin) (I)

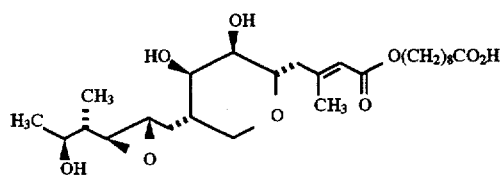

to monic acid A (II)

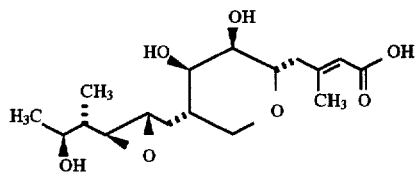

or the conversion of pseudomonic acid C (III)

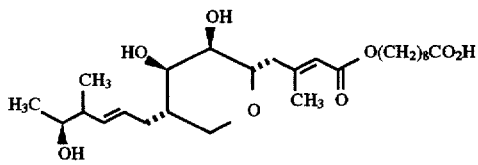

or its methyl ester to monic acid C (IV)

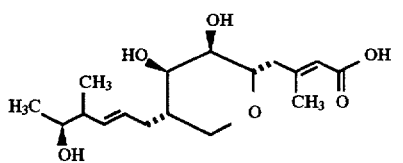

Monic acids are useful as a starting materials for producing biologically active compounds in particular pharmaceuticals. Beecham Group plc GB 1 587 058 describes the chemical preparation of monic acid. One problem with chemical methods of preparation has been that of extracting the product.

There is a requirement for an alternative to chemical hydrolysis of pseudomonic acids to monic acids. Although a large number of hydrolytic enzymes are known, surprisingly we have found that none of 60 or so commonly available animal, plant and microbial hydrolases (for example from Sigma Chemical Company, Poole, Dorset) tried to date have been found to have suitable activity. For example subtilisin E.C. 3.4.21.14 was found not to hydrolyse a 9-hydroxynonanoate ester from an analogue of pseudomonic acid A (Sime et al. 1987, Tet. Lett. 28(43), pp 5169–72).

Freer et al (Synthesis and Applications of Isotopically labelled compounds(1988), Proceedings 3rd International symposium, Elsevier) used a mammalian enzyme (hog liver esterase) to convert [2-$^{14}$C] mupirocin to [2-$^{14}$C] monic acid. We have also found that this does not provide the required level of activity.

We have now found that enzymes suitable for use in the process of the invention can be derived from certain Actinomycetes in particular Kitasatosporia, Kibdelosporangium sp. and certain Streptomyces sp.

Accordingly, the present invention provides a process for the production of monic acids which comprises contacting the corresponding pseudomonic acid or an ester thereof with a hydrolase enzyme from a suitable microorganism.

By esters of pseudomonic acid we include those which are cleavable by the hydrolase enzyme of the invention to produce the corresponding monic acid. Suitable esters include (C1–C6) esters, particularly methyl esters.

The present invention also provides a method of screening for microorganisms capable of transforming pseudomonic acid into monic acid by incubating said organisms with pseudomonic acid and assaying for the loss of antibacterial activity compared to a pseudomonic acid standard.

Particularly suitable microorganisms include S. lividans in particular S. lividans NCIMB 11416, S. griseofuscsus ATCC 23916 and S. ambofaciens ATCC 23873 and Kibdelosporangium aridum ATCC 39922. The strain Kitasatosporia NCIMB 40568 is a novel microorganism and as such forms a further aspect of the present invention. This strain has been deposited at the National Collection of Industrial and Marine Bacteria (NCIMB), Aberdeen, Scotland under accession number NCIMB 40568 on 14 Jun. 1993.

Kitasatosporia sp. NCIMB 40568 is grey sporing and has the following characteristics: cell wall peptidoglycan: LL-A$_2$pm/meso- A$_2$pm [Buchanan, R. E. and Gibbons, N. E. Bergey's manual of Determinative Bacteriology].

The medium for cultivating the microorganisms according to the invention suitably contains sources of assimilable carbon and nitrogen together with inorganic salts. Suitable sources of nitrogen include cornsteep liquor, yeast extract, soyabean flour, meat extract, cottonseed, flour, malt, distillers dried solubles, amino acids, protein hydrolysates and ammonium and nitrate nitrogen. Suitable carbon sources include glucose, lactose, maltose, starch, glycerol and treacle eg. Fowler's.

Suitably the culture medium also includes alkali metal ions (for example, sodium) halogen ions (for example chloride) and alkali earth metal ions (for example calcium and magnesium) as well as trace elements such as iron and cobalt Suitably the cells are harvested by centrifugation or filtration.

The biotransformation/process of the present invention can be carried out using whole cells, cell free extracts permeabilised cell or the isolated enzyme from the microorganisms or any of these in immobilised form.

Where the biotransformation is carried out using whole cells, the microorganism may be in the form of a growing culture, resting culture, washed mycelium, immobilised cells or protoplasts.

When cell-free extracts are used these are suitably produced by shear and/or chemical or enzymic lysis or other methods of disruption, preferably sonication, and optionally thereafter removing cell debris, leaving the enzyme activity in solution.

The enzyme is suitably prepared according to the examples below. The enzyme may be prepared by culturing the microorganism in a conventional manner, especially under aerobic conditions in a suitable liquid or semi-solid medium.

The culture conditions may be a temperature in the range from 5°–50° C. and pH in the range 3 to 9, preferably 6–8, most preferably 7.2.

The enzyme may be isolated and used in purified form, partially purified form, as obtained in an impure state, as a filtrate from a disrupted cell preparation, or as a crude cell homogenate. Most suitably the enzyme is, for example, at least purified to remove other enzymes which might also catalyse the destruction of the starting material or the enzyme.

In a further aspect of the invention there is provided an enzyme capable of hydrolysing pseudomonic acid to monic acid obtainable by treating mycelium from Streptomyces/ Kitasatosporia/Kibdelosporangium according to example 5 and/or 7, (and 6) below, by centrifugation and cell disruption (ultrasonication) followed by fractionation and chromatography.

Most suitably the enzyme is immobilised for example to an insoluble support material such as by the procedures discussed by Powell (1990) in Microbial Enzymes and Biotechnology ed. Fogarty & Kelly p369–394. This provides the advantage of increased yield and throughput.

The starting material pseudomonic acid can be prepared by the method described in GB 1,395,907.

When the biotransformation is carried out using whole cells, the incubation medium comprises resting cell medium: $KH_2PO_4$ 2 g, $K_2HPO_4$ 1.5 g, KCl 0.2 g, Mg $Cl_2.6H_2O$ 0.2 g, $Na_2SO_4.10H_2O$ 0.22 g, glucose 1.0 g in a litre of deionised water pH 6.5 or a water system with pH adjustment.

When the biotransformation is carried out using cell free extracts the incubation medium comprises a suitable buffer.

In addition to substrate the enzyme reaction mixture may contain one or more other cofactors eg metal ions or stabilisers, for example thiols.

The process of the invention may suitably be carded out in aqueous media, the reaction mixture suitably being maintained in the range pH 4–9, more suitably from 6 to 8, preferably around 7.2 e.g pH 7.4. The pH is suitably controlled using buffers or preferably by the addition of acid or base titrant. The temperature of the reaction should generally be in the range, preferably 5°–50° C. preferably 22°–45° C., most preferably 32°–37° C.

Alternatively the reaction can be carded out in organic solvents or in the presence of organic solvents eg. acetone, methyl isobutyl ketone (MIBK).

The reaction time depends on such factors as concentrations of reactants and cofactors, temperature and pH.

After the reaction is complete the product can be isolated by conventional methods and as shown in the examples below. The initial purification conveniently involves a chromatography step.

The following examples illustrate the invention.

EXAMPLE 1

Screening and Assay Methods

1.1 Primary Screen

A biotransformation would be accompanied by a loss in antibacterial activity therefore this was used as the basis for an asssay to identify microorganisms that could transform pseudomonic acid to monic acid. 3×1 ml volumes of G1 medium (Example 2) dispensed into 24 well microtitre plates were inoculated (eg with actinomycete mycelial growth from agar plates ) and incubated at 28° C. with shaking for 4 days. An uninoculated control plate was also incubated (containing just G1 media). Pseudomonic acid was added at 0.05 mg/ml to the plates and the plates re-incubated for 24 h. 50 μl of culture (duplicate) were then added to a bioassay plate containing a suitable pseudomonic acid sensitive strain eg *Staphylococcus aureus* (eg V573) or *E. coli* (eg ESS strain). Zones of inhibition were measured after overnight incubation at 37° C.

1.2 Secondary Screen

Incubations were carded out with increased concentrations of substrate to find cultures capable of the required transformation at a higher substrate concentration. Flasks (500 ml) containing 100 ml G1 medium (Example 2) were each inoculated with 1.5 ml inoculum of culture/mycelium in 0.02% Tween 80 in water. The flasks were shaken (240 rpm) for 4 days at 28° C. then the contents were centrifuged and resuspended in resting cell medium (example 2). To compensate for the variable density of growth the cultures were resuspended between 2 and 6× broth density (original cell density obtained after growth is equivalent to 1× broth cell density). Pseudomonic acid (10 mg/ml) in 0.05M $NaH_2PO_4$ pH 7.0 was added after filter sterilisation to each flask to give a final concentration of 0.5 mg/ml. After shaking for 24 h at 28° C. the contents of the flask were centrifuged, the supernatant volumes measured and an aliquot was taken for hplc analysis (Example 2).

Particularly good results were obtained with two cultures: Kitasatosporia NCIMB 40568 (87% conversion to monic acid, broth cell density of 2) and *Kibdelosporangium aridum* ATCC 39922 (76.9% conversion, broth cell density of 2). Comparable results were also obtained with *Streptomyces lividans* NCIMB 11416. Further incubations at substrate concentrations of 2 and 5.5 mg/ml were also carried out with a small number of the positive cultures.

1.3 Extraction and Analysis

Extractions were carded out by adding NaCl to saturate the supernatant which was cooled (0°–5° C.) and the pH altered to 3.0 using 5M HCl. Ethyl acetate was used for the solvent extraction (3×⅓ volumes) then dried with Mg $SO_4$ and filtered prior to rotary evaporation. A small volume (0.5 ml) was left in the cold overnight to produce crystals which were then dried. Purity assay by hplc (Example 2) and $^1$HNMR confirmed the structure to be monic acid.

For the $^1$HNMR (250 MHz) analysis samples were run in deuterated DMSO and compared to the monic acid standard.

EXAMPLE 2

Whole Cell Reaction Using Kitasatosporia Sp.

A mycelial suspension of Kitasatosporia sp. NCIMB 40568 in 1.5 ml water containing 0.02% Tween 80 was used to inoculate a 500 ml Erlenmeyer flask containing 100 ml G1 medium. G1 medium consists of:-dextrin 30 g, Fowler's treacle 20 g, bacteriological peptone 7 g, in a litre of deionised water adjusted to pH6.8. The flask was shaken for 4 days at 28° C. after which the broth was centrifuged and resuspended to 25 ml in a resting cell medium ($KH_2PO_4$ 0.5 g, $K_2HPO_4$ 1.5 g, KCl 0.2 g, Mg $Cl_2.6H_2O$ 0.2 g, $Na_2SO_4.10H_2O$ 0.22 g and glucose 1.0 g in a litre of deionised water adjusted to pH 6.5) in a 250 ml flask. Pseudomonic acid (10 mg/ml) in 0.05M $NaH_2PO_4$ (pH 7.0) was added to give a final concentration of 500 μg/ml.

After shaking for 24 h at 28° C., the content of the flask was centrifuged and an aliquot was analysed by HPLC (HPLC assay:-C18 column 4.6×250 mm, 30% MeOH/ 0.05M NaH$_2$PO$_4$ pH 4.8, 230 nm, 1.5 ml/min. Monic acid Rt=4.9 mins) This confirmed an 87% conversion of the substrate to monic acid. 'HNMR analyses (250 MHz) were carded out to confirm the structure to be monic acid.

EXAMPLE 3

Cell Free Reaction Using Kitasatosporia Sp.

Kitasatosporia sp. NCIMB 40568 was inoculated into a flask containing G1 medium as described above in example 2, and the flask shaken for 48 h at 28° C. From this seed flask 2 ml portions of broth were used to inoculate six further flasks each containing 100 ml of G1 medium. The flasks were shaken for 72 h at 28° C. after which the broth was centrifuged, discarding the supernatant, and the cells resuspended to 60 ml in 0.2M Tris/HCl buffer pH 7.4. The cells were disrupted in 10 ml batches using ultrasonication (MSE Soniprep, 5 cycles of 20 seconds on, 40 seconds off) and this broken cell suspension was centrifuged and the supernatant retained. To 250 µl of the cell supernatant was added 250 µl of pseudomonic acid solution (8 mg/ml in 0.3M Tris/HCl buffer pH 7.4). The reaction was incubated for 24 h at 37° C. with shaking Methanol (500 µl) was then added, and the mixture cooled in ice for 10 minutes. The precipitated protein was removed by centrifugation, and the supernatant assayed for monic acid as described in example 2. Monic acid was identified with a substrate conversion of 92%.

EXAMPLE 4

Cell Free Reaction Using S. lividans

Streptomyces lividans NCIMB 11416 was cultured as described in example 3, using a seed flask to inoculate five production flasks each containing 100 ml of G1 medium. The cells were disrupted as described in example 3, first resuspending the cells obtained from the broth to 38 ml in 0.2M Tris/HCl buffer (pH 7.4). To 250 µl of the cell supernatant was added 250 µl of pseudomonic acid (2 mg/ml in 0.2M Tris/HCl pH 7.4 buffer). The reaction was incubated with shaking for 24 h at 28° C. The reaction was stopped as described in example 2 and assayed for monic acid by HPLC. Monic acid production was identified with a substrate conversion of 59%.

EXAMPLE 5

Hydrolysis Using a Semi Purified Enzyme Preparation from Kitasatosporia sp. NCIMB 40568.

Kitasatosporia sp. NCIMB 40568 was cultured as described in example 3 and the mycelial pellet from 500 ml of growth medium was resuspended to 50 ml in 0.2M Tris/HCl buffer (pH 7.4) prior to ultrasonic disruption as described. The recovered supernatant was treated with 5 mM dithiothreitol and 1% w/v of streptomycin sulphate and then stored at 0° C. for 30 minutes. Centrifugation was followed by removal of 41 ml of supernatant to which was added ammonium sulphate (9.16 g) over 5 minutes whilst gently stirring at 0° C. After stirring for a further 15 minutes the sample was centrifuged and the supernatant retained. To this supernatant (43 ml) was added ammonium sulphate (5.3 g) in a similar manner.

A 9 ml potion of the resulting suspension was centrifuged and the pellet retained to be redissolved in 2.5 ml of a mixture containing 0.1M NaCl, 10% w/v glycerol and 1 mM dithiothreitol. After desalting by gel filtration the preparation was stored at −20° C.

A 1 ml aliquot of this protein preparation was thawed and diluted with 0.2M sodium chloride solution (1.0 ml), and the pH of the resulting solution adjusted to 7.01 by the addition of 0.01M sodium hydroxide solution. To this stirred solution, at 30° C., was added a solution of pseudomonic acid (2 mg in 0.78 ml deionised water at pH 7.4) and the pH of the resulting mixture was maintained at 7.4 by the addition of 0.01M sodium hydroxide solution.

Monitoring of base addition indicated a conversion of 82% pseudomonic acid to monic acid after 5 hours and at this stage HPLC indicated a conversion of 88%. After 10 hours a one molar equivalent of base had been added to the reaction mixture and the pH stabilised indicating the reaction had stopped. HPLC assay at the end of the reaction indicated a 96% conversion to monic acid.

EXAMPLE 6

Conversion of Pseudomonic Acid to Monic Acid using an Immobilised Preparation from Streptomyces lividans NCIMB 11416

Spores of S. lividans NCIMB 11416, stored in 20% sucrose at −70° C., were inoculated into five 1 litre flasks each containing 400 ml of a medium containing 25 g yeast extract, 2 g NaH$_2$PO$_4$.2H$_2$O, 1 g MgSO$_4$.7H$_2$O, 0.01 g MnSO$_4$.4H$_2$O, 0.01 FeSO$_4$.7H$_2$O, 0.08 g CaCl$_2$.2H$_2$O and 15 g glycerol per litre (pH 6.8). These flasks were incubated for 48 hours at 30° C. in an orbital shaking incubator and then combined into an inoculum can prior to inoculation of 800 liters of DFO3A medium (27.5 g yeast extract, 33 g glycerol, 2.2 g NaH$_2$PO$_4$.2H$_2$O, 5 g MgSO$_4$.7H$_2$O, 0.01 g MnSO$_4$.4H$_2$O and 1 g Foamaster TDB1 (Henkel) per litre, pH6.8) in a 1000l capacity standard configuration fermenter with disc turbine agitators. Initial running conditions were 250 rpm, 30° C., 15 psi head pressure, air flow of 40 m$^3$/hr, pH controlled at 6.8 with ammonia. During the run the dissolved oxygen level was kept above 5% of the saturation value by increasing agitation to 300 rpm, increasing air flow to 80 m$^3$/hr and increasing head pressure to 20 psi. After 38 hours the vessel was chilled to approximately 5° C. while reducing the air flow and agitation rate slowly.

The broth was reduced in volume to ca 120 l by passage through a desludging centrifuge (Westphalia Model SAMR5036, flow rate 10–20/(min). 40 l of this concentrated mycelial paste was homogenised by passage through a homogeniser (APV Manton-Gaulin LAB 60 model, 10,000 psi at 1 litre/min), maintaining the temperature below 30° C. The homogenate was partly clarified by addition of 40 l of 0.1M NaH$_2$PO$_4$ (pH 7.0) and passage through the desludging centifuge. The supernatant (80 l) was reduced in volume to ca. 25 l using a DDS M38 ultrafiltration unit. 8 l of this material was made up to 0.5% polyethyleneimine with a solution of 90 g polyethyleneimine in 1 litre H$_2$O, adjusted to pH 7.8 with 2M H$_3$PO$_4$ prior to addition to the S. lividans extract. After stirring at room temperature for 15 minutes the mixture was centrifuged at 4600 rpm (Mistral 6000 centifuge, 1 l bottles) for 20 mins and the pellet was discarded. The supernatant was adjusted to 65% of saturation level with ammonium sulphate. After 15 minutes the precipitate was recovered by centrifugation (same conditions as above) and resuspended in 3 l of 0.1M phosphate buffer (0.039M NaH$_2$PO$_4$, 0.061M Na$_2$HPO$_4$, pH7.0).

The enzyme solution was diluted with 0.5 l of 0.1M phosphate buffer (pH7.0) and 200 g of (NH$_4$)$_2$SO$_4$ was added to increase the conductivity to 40 mS. 400 g of Duolite A568 resin (Röhm and Haas, Chauny, France) was added (31 mg protein per g of resin) and the mixture was stirred overnight, controlling pH at 7.0 with 1M NaOH, to allow adsorption of hydrolase enzyme. The enzyme-resin was recovered by filtration, washed on the filter with 200 ml of distilled H$_2$O and added to 3.5 l of 0.2% glutaraldehyde in 0.1M phosphate (pH7.0). The mixture was stirred for 1 hour, the enzyme-resin was recovered by filtration and added to 3.5 l of 0.1M phosphate buffer pH7.0. This mixture was stirred for 1 hr, the enzyme-resin was recovered by filtration and stored damp at 4° C.

250 g of enzyme-resin was added to 1 litre of 0.25% pseudomonic acid and the mixture was stirred at 32° C., maintaining the pH at 7.4 with 1M NaOH. After 24 hours the enzyme-resin was recovered by filtration. The filtrate was analysed by HPLC for monic acid (HPLC assay: 10μ C18 column (3.9×300 mm, Bondapak), 30% methanol, 0.05M NaH$_2$PO$_4$, pH3.8, 1.5 ml/min, Rt=4.5 min) and for pseudomonic acid (HPLC assay: 10μ C18 column (3.9×300 mm, Bondapak), 67% methanol, 0.06M ammonium acetate, pH6.3, 1.5 ml/min, Rt=5.5 min). The analysis showed that no pseudomonic acid remained in solution and the molar yield of monic acid was 63%. The enzyme-resin was re-used 3 more times although the time taken for the pseudomonic acid to disappear increased with each repeat reaction to a time of 96 hours for the fourth enzymation reaction. The average yield of monic acid over the four enzymations was 80%.

The solution of monic acid from the first enzymation was chilled to 2° C. and saturated with 300 g sodium chloride. 5M HCl was added drop-wise to adjust the pH to 3.0. Ethyl acetate (350 ml) was added and the mixture was stirred vigorously for 5 min before separation. The aqueous layer was extracted twice more with 350 ml ethyl acetate. The ethyl acetate extracts were combined, dried over MgSO$_4$, concentrated to 150 ml using a rotary evaporator (maintaining temperature at below 30° C.), stirred in an ice bath until precipitation occurred and then stored at 2° C. overnight.

The product was filtered, washed with ethyl acetate, dried under vacuum and analysed by HPLC and $^1$H NMR. The analyses confirmed that the product was monic acid. 0.6 g of monic acid was recovered (55% extraction yield).

EXAMPLE 7

Purification of Hydrolase from *S. lividans* NCIMB 11416

8 l of ultrafiltration concentrate (Example 6) was treated with deoxyribonuclease (Sigma DN-25, 320 mg), left for 1h at 4° C., and centrifuged (6,000×g, 30 min., 4° C.). The separated supernatant was brought to a 30% saturation level of ammonium sulphate (Sigma grade III) by the addition of the solid while stirring. The suspension was left for 15 min. and then centrifuged (6,000×g, 30 min., 4° C.). The precipitate was removed by vacuum filtration (Whatman GF/D filter paper). To the filtrate, ammonium sulphate was added to attain an 80% saturation level. After 15 min., the suspension was centrifuged (17,700×g, 25 min., 5° C.). The precipitate was retained after decanting the supernatant.

The precipitate was then largely solubilised, by adding 1M ammonium sulphate in 50 mM di-sodium hydrogen phosphate pH 7.0 buffer to achieve a volume of 2.5 l, and then distilled water to a final volume of 5.0 l. This gave an equivalent conductivity level to that of 1M ammonium sulphate in 50 mM di-sodium hydrogen phosphate pH 7.0 buffer. This preparation was applied to a hydrophobic interaction resin column (Butyl Agarose 6 X L, Affinity Chromatography Ltd), 8.0 cm×9.0 cm, previously equilibrated in the above buffer, and run at room temperature.

The column was washed with the same buffer and eluted using a step gradient of diminishing ammonium sulphate concentrations in 50 mM phosphate buffer, down to 0.1 M ammonium sulphate. Column fractions were assayed for esterase activity by adding a 50 μl sample to 450 μl of pseudomonic acid A (2 mg/ml in 0.2M Tris/HCl buffer pH 7.4). The reaction was incubated for 1 h at 37° C., and methanol (500 μl) was added. The mixture was cooled in ice for 10 min and the precipitated protein removed by centrifugation. The supernatant was assayed for monic acid as described in example 2. Protein concentrations were determined by the Bradford method (Anal. Biochem., 1974, 72,248–254).

The active fractions were bulked to get 1500 ml and ultrafilter (Amicon YM30) concentrated to 800 ml. This concentrate was dialysed (Spectropore 4) overnight at 4° C. against 5 l of a buffer consisting of 50 mM disodium hydrogen phosphate pH 7.0 containing 0.5M sodium chloride and 10% v/v glycerol. The solution was applied to a metal chelate affinity resin column (Chelating Sepharose Fast Flow, charged with copper ions, Pharmacia). 19.0 cm×2.6 cm, previously equilibrated in the latter buffer. The load was washed with this buffer and then a linear gradient applied using the buffer with elevating ammonium chloride concentrations of 0–1M. Column fractions were assayed for esterase activity in a similar manner to that described previously. Active eluent fractions were pooled (110 ml) and the ultrafilter (YM30) concentrated to 15 ml. While ultrafiltering, portions of a further buffer (25 mM Bis Tris Propane pH 7.0 in 10% v/v glycerol) were introduced as a buffer exchange.

The concentrate was applied to an union exchange column (Resource Q, 1 ml, Pharmacia) previously equilibrated in the above buffer. Following washing, a linear elution gradient was applied with this buffer containing increasing concentrations of sodium chloride from 0–1M. Enzyme activity assays indicated three active fractions in the eluent.

Analysis of the active fractions by SDS-polyacryalamide gel electrophoresis (Phast Gel, Pharmacia, gradient 10–15%) using a Coomassie Blue Stain indicated a homogeneous protein with its peak concentration in the middle fraction, correlating with maximal enzyme activity. This data was endorsed by reverse phase hplc analysis (eluent= gradient of 0–80% methanol in 0.08% trifluoroacetic acid, λ=215 nm).

Protein assay of the active fractions indicated a total of 0.5 mg protein (BSA standard).

EXAMPLE 8

Determination of Molecular Weight of the Hydrolase of *S. lividans* NCIMB 11416

The fraction of highest activity in the final ion exchange purification (Example 7) gave one peak on reverse-phase HPLC (RP-HPLC). This material was analysed by Laserdesorption mass spectrometry (LD-MS) on a Finnigan Lasermatt instrument and the total molecular weight (by LD-MS) was 54048 (+−200) daltons.

We claim:

1. An enzyme which hydrolyzes pseudomonic acid to monic acid, the enzyme obtained by treating mycelium from *Streptomyces lividans* NCIMB 11416, by centrifugation and cell disruption followed by fractionation and chromotagraphy.

2. An enzyme as claimed in claim 1 having a molecular weight of approx. 54,000 daltons.

3. An enzyme which hydrolyzes pseudomonic acid to monic acid, the enzyme obtained by treating mycelium from Kitosatosporia sp. NCIMB 40568, by centrifugation and cell disruption followed by fractionation and chromatography.

* * * * *